(12) United States Patent
Birkbeck et al.

(10) Patent No.: US 8,500,743 B2
(45) Date of Patent: Aug. 6, 2013

(54) SURGICAL JIG

(75) Inventors: Alec Birkbeck, Leeds (GB); James Brooks, Leeds (GB); Andrew Burton, Leeds (GB)

(73) Assignee: Depuy International Limited (GB)

( * ) Notice: Subject to any disclaimer, the term of this patent is extended or adjusted under 35 U.S.C. 154(b) by 0 days.

(21) Appl. No.: 13/141,103

(22) PCT Filed: Dec. 16, 2009

(86) PCT No.: PCT/GB2009/051722
§ 371 (c)(1),
(2), (4) Date: Sep. 12, 2011

(87) PCT Pub. No.: WO2010/073029
PCT Pub. Date: Jul. 1, 2010

(65) Prior Publication Data
US 2011/0319901 A1   Dec. 29, 2011

(30) Foreign Application Priority Data

Dec. 22, 2008   (GB) .................................. 0823298.5

(51) Int. Cl.
*A61B 17/56* (2006.01)
(52) U.S. Cl.
USPC ................................................ 606/87; 269/6
(58) Field of Classification Search
USPC ................. 606/87, 88, 89; 269/3, 6, 143, 249
See application file for complete search history.

(56) References Cited

U.S. PATENT DOCUMENTS

2002/0193801 A1* 12/2002 Marchione et al. ............. 606/96
2008/0215057 A1*  9/2008 Willi et al. ...................... 606/88

FOREIGN PATENT DOCUMENTS

| WO | WO 2004107993 A1 | 12/2004 |
| WO | WO 2005027755 A1 | 3/2005 |
| WO | WO 2005082259 A1 | 9/2005 |
| WO | WO 2009001109 A1 | 12/2008 |
| WO | WO 2009098086 A1 | 8/2009 |

OTHER PUBLICATIONS

PCT International Search Report and Written Opinion PCT/GB2009/051722 Apr. 29, 2010.
UK Search Report GB0823298.5 dated Apr. 1, 2009.

* cited by examiner

*Primary Examiner* — Kevin T Truong
*Assistant Examiner* — Christian Sevilla

(57) ABSTRACT

A surgical jig for determining an axis extending into the end of a bone (2). The jig comprises a platform (10) arranged to be supported upon a resected surface (4) at an end of a bone (2), first and second clamps (16) and an alignment guide (18). The first and second clamps (16) are coupled to the platform (10) and are arranged to engage first and second portions of a bone lip (6) extending around at least part of the resected surface (4) to secure the platform (10) to the resected surface (4). The alignment guide (18) defines an axis extending into the end of the bone (2), the alignment guide (18) being pivotally coupled to the platform (10). A method of determining an axis extending into the end of a bone (2) using the surgical jig is also disclosed. The method comprises resecting the end of a bone (2) to leave a bone lip (6), coupling the surgical jig to the resected end of the bone (2), and pivoting the alignment guide (18) until the alignment guide (18) coincides with a required axis extending into the end of the bone (2).

15 Claims, 2 Drawing Sheets

SURGICAL JIG

CROSS REFERENCE TO RELATED APPLICATION

This application is a National Stage application under 35 U.S.C. 371 of International Patent Application PCT/GB2009/051722 filed Dec. 16, 2009.

BACKGROUND OF THE INVENTION

The present invention relates to a jig and in particular to a surgical jig for use in determining an axis of a body part. More particularly, the surgical jig may be used for determining an axis extending into the end of a bone, and in particular a long bone such as a femur or a humerus.

For many surgical procedures and operations it can be necessary to determine an axis of a body part having a complex, often non-uniform, geometry. This can be achieved by the surgeon visually assessing the body part to determine where, and at what angle, to start drilling, cutting or carrying out any other invasive surgical procedure. This approach is limited in its accuracy and its successful utilisation can be highly dependent on the skill and experience of the surgeon. The results of a badly carried out procedure can be exacerbated in surgical procedures in which a correct determination of the axis position is important in order to ensure the correct mechanical functioning of the body part in the overall mechanical functioning of the body.

In the area of orthopaedic implants, if an axis is incorrectly determined intra-operatively then the implant can be incorrectly positioned which can give rise to various difficulties such as incorrect patient limb motion, pain, incorrect mechanical functioning of the implant, excessive wear of the implant and further damage to the body part. Therefore it would be desirable to be able to provide a device for assisting in the accurate determination of an axis of a body part.

An example of a situation in which it is important to accurately determine an axis of a body part intra-operatively is during the implantation of a prosthetic hip joint. It will be appreciated however that similar considerations are equally applicable to the implantation of other orthopaedic implants, for instance the humeral component of a shoulder joint. Hip prostheses are generally formed from two components: an acetabular, cup which lines the acetabulum, and a femoral component which replaces the femoral head. To implant the femoral component, the femoral head of the bone is shaped to receive the prosthesis. A stem part of the femoral component is inserted into the bore.

It is important that that the bearing surface of the femoral component is accurately positioned to mimic the original bone bearing surface. This requires that the hollowed cavity to receive the stem part of the femoral component is accurately aligned for both angular orientation and translational position within the femur. As an initial step it is known to use a surgical jig coupled to the head of the femur in order align a guide pin inserted into the head of the femur. Typically the guide pin is inserted along the femoral neck axis or at a predetermined offset to the femoral neck axis.

Known surgical jigs for implanting a guide pin into the head of a femur comprise a tripod arrangement in which three or more legs extend around the femoral head and clamp onto the sides of the femoral neck. Coupled to the legs is an alignment guide comprising a tube for positioning and inserting the guide pin into the femoral head. The desired position of the pin can be determined from pre-operative analysis of x-rays of the joint. The guide pin is left protruding from the femoral head to guide further surgical steps. A cannulated drill may be used to drill a bore into the end of the bone along the femoral neck axis guided by the guide pin. The drilled bore may then be used to guide a resection of the femoral head, ensuring that the resection is at a predetermined orientation relative to the femoral neck axis.

However, known surgical jigs based upon a tripod arrangement supported upon the surface of the femoral head can be unstable. Partly, this instability may be due to the location of clamping to the femoral neck being remote from the point of entry of the guide pin into the femoral head. Furthermore, as the position of the tripod is adjusted, the axis of the alignment guide coupled to the tripod shifts about a centre of rotation within the centre of the femoral neck between the clamps. This is undesirable as it results in the axis of the alignment guide upon the surface of the femoral head simultaneously changing angular orientation and translating across the surface of the bone.

It is an object of embodiments of the present invention to obviate or mitigate one or more of the problems associated with the prior art, whether identified herein or elsewhere. In particular, it is an object of embodiments of the present invention to provide an improved surgical jig which is arranged to couple to the end of a long bone to provide a more stable platform for determining an axis extending into the end of the bone. Furthermore, it is an object of embodiments of the present invention to provide a surgical jig incorporating an alignment guide for inserting a guide pin into the end of the bone in which the angle and position of the insertion point of the guide pin may be separately controlled.

BRIEF SUMMARY OF THE INVENTION

According to a first aspect of the present invention there is provided a surgical jig for determining an axis extending into the end of a bone, the jig comprising: a platform arranged to be supported upon a resected surface at an end of a bone; first and second clamps coupled to the platform arranged to engage first and second portions of a bone lip extending around at least part of the resected surface to secure the platform to the resected surface; and an alignment guide defining an axis extending into the end of the bone, the alignment guide being pivotally coupled to the platform.

An advantage of the first aspect of the present invention is that the platform of the surgical jig is supported upon a resected surface which increases the stability of the platform relative to a platform mounted upon a convex bearing surface at the end of the bone. Consequently, the alignment guide may be accurately positioned to define the angular orientation of an axis extending into the end of the bone with a reduced risk of subsequent movement. The alignment guide can be used to place a pin extending into the end of the bone. The clamps engage a bone lip extending around at least part of the resected surface and firmly secure the platform upon the resected surface. If the bone lip is to be removed during subsequent surgical steps then it is immaterial whether the clamps cause damage to the bone lip The clamps may comprise hooks coupled to the platform and arranged to engage an underside of the bone lip, the bone tapering away from the resected surface to define the bone lip. The first and second clamps may be coupled together via at least one rail which is arranged to pass over the resected surface of the bone and is adjustable in length to draw the clamps together to engage the bone lip, and wherein the platform may be slidably coupled to the at least one rail such that the insertion point of the defined axis into the end of the bone can translate across the resected surface. The at least one rail may comprise a ratchet for drawing the clamps together such that the clamps are arranged to apply compressive force to the underside of the bone lip.

The alignment guide may comprise a tube arranged to receive a guide pin passing through the alignment guide into the end of the bone along the defined axis. The alignment guide may be coupled to the platform such that when the surgical jig is coupled to a resected end of a bone the centre of rotation of the defined axis is positioned upon the resected surface.

The platform may comprise a bore extending through the platform to the resected surface and the jig may further comprise a foot slidably received within the platform bore and arranged to rest against the resected surface, the foot being coupled to the alignment guide via a cannulated ball joint such that the alignment guide can pivot about first and second orthogonal axes extending through the centre of rotation of the alignment guide and a guide pin can pass through the ball joint from the tubular alignment guide into the end of the bone. The foot may be arranged to slide across the resected surface of the bone within the platform bore when the alignment guide pivots relative to the platform about the centre of rotation of the alignment guide.

The surgical jig may further comprise a locking guide frame arranged to lock the alignment guide to the platform to selectively prevent further rotation about the first and second axes. The guide frame may comprise a first slot through which the alignment guide passes, the first slot restricting movement of the alignment guide to rotation about the first axis. The portion of the guide frame defining the first slot may be curved and defined by a constant radius of curvature extending from the centre of rotation of the alignment guide. The surgical jig may further comprise a threaded sleeve surrounding the alignment guide and passing through the first slot and a first locking nut arranged to engage the threaded sleeve such that edge portions of the first slot can be trapped between a flange upon the threaded sleeve and the first locking nut to prevent further rotation of the alignment guide about the first axis.

The guide frame may further comprise a second slot arranged to engage a pin extending from the platform such that the guide frame is slidably coupled to the platform and sliding motion of the second slot over the pin causes the alignment guide to rotate about the second axis. A centre line of the second slot may be curved and defined by a radius of curvature equal to the distance from the centre of the second slot to the resected surface of the bone. The pin may comprise a threaded portion and the surgical jig may further comprise a second locking nut arranged to engage the threaded portion of the pin such that edge portions of the second slot can be trapped between the platform and the second locking nut to prevent further rotation of the alignment guide about the second axis.

The alignment guide may further comprise a lug and the threaded sleeve may further comprise a slot arranged to pass over the lug, the surgical jig further comprising a third locking nut arranged to engage the threaded sleeve and to bear against the lug such that when the jig is coupled to the resected end of a bone the foot presses against the resected surface.

According to a second aspect of the present invention there is provided a method of determining an axis extending into the end of a bone, the method comprising: resecting the end of the bone to leave a bone lip extending around at least part of the resected surface; coupling a surgical jig to the resected end of the bone, said coupling comprising: supporting a platform upon the resected surface; and engaging first and second portions of the bone lip with first and second clamps coupled to the platform to secure the platform to the resected surface; and pivoting an alignment guide pivotally coupled to the platform, the alignment guide defining an axis extending into the end of the bone until the alignment guide coincides with a required axis extending into the end of the bone.

The alignment guide may comprise a tube extending to the resected surface of the bone, and the method may further comprise inserting a guide pin into the resected surface of the bone at a required insertion point and sliding the alignment guide over the guide pin prior to coupling the surgical jig to the end of the bone.

The method may further comprise driving the guide pin into the bone along the axis defined by the alignment guide.

BRIEF DESCRIPTION OF THE DRAWINGS

An embodiment of the present invention will now be described, by way of example only, with reference to the accompanying drawings in which.

DETAILED DESCRIPTION OF THE INVENTION

Figure 1:
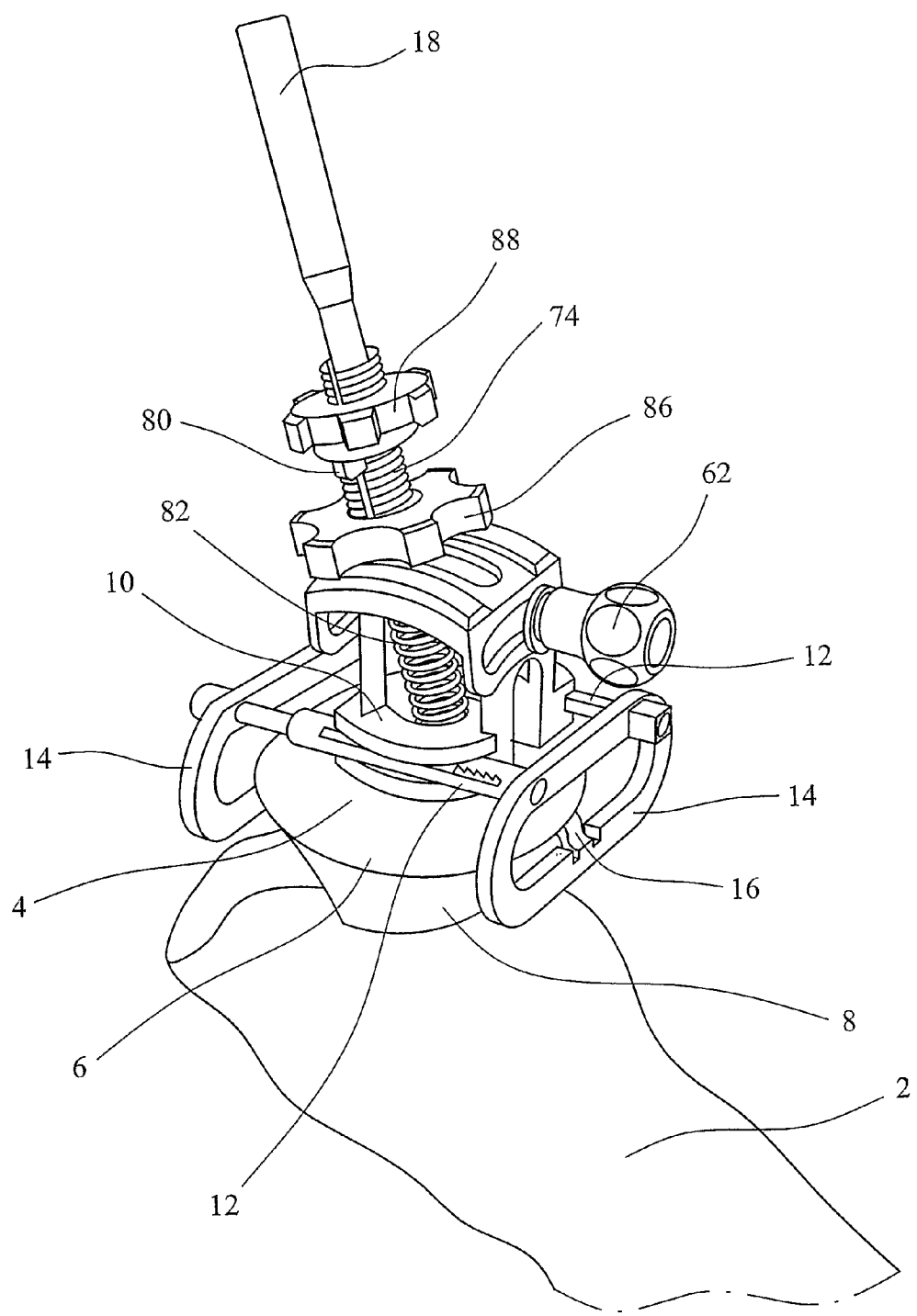
FIG. 1 illustrates a surgical jig in accordance with an embodiment of the present invention coupled to a resected end of a femur.

Embodiments of the present invention provide a surgical jig which is arranged to be mounted upon a resected surface at the end of a long bone. For instance, the long bone may be a femur. During a hip replacement operation, in order to implant a femoral prosthetic component into the end of the femur it is typically necessary to resect most or all of the femoral head. Currently, this resection is performed after the initial alignment steps to determine the neck axis of the femoral component have been completed upon the natural femoral head. The present inventors have realised that problems associated with known surgical jigs for determining the neck axis of the femoral component are at least partly due to instability of the surgical jig upon the femoral head. Furthermore, the present inventors have recognised that by performing an initial rough cut resection prior to determining the neck axis, a resected surface may be provided at the end of the bone which provides a more stable surface for mounting the surgical jig. The rough cut resection may be performed by visual inspection. There is no requirement for the resection to be accurately aligned relative to the femoral neck axis. The only requirement is that the rough cut resection is performed sufficiently close to the end of the femur that the final accurate resection of the bone will remove the whole of the rough cut resected surface.

Advantageously, performing an initial resection in this way allows the bulk of the femoral head to be removed to allow access to the acetabular region, which must also be operated upon to receive an acetabular cup. The rough cut resection is positioned approximately at the junction between the femoral head and neck. The resected surface is at least partially surrounded by a lip of bone at the head/neck junction. The initial resection may be performed freehand using an oscillating saw.

A surgical jig in accordance with the present invention couples to the resected surface using clamps which hook onto the bone lip. The clamps are coupled together by a platform which rests upon the resected surface. The clamps are releasable allowing the jig to be repositioned if required. Advantageously, the clamps engage only the bone lip and do not extend onto the outer surface of the neck itself. The surface of the neck is irregular and sensitive to damage caused by known surgical jigs which clamp directly onto the neck. It is desirable to avoid damage to the neck for femoral prosthetic components for which part or all of the original femoral neck is preserved. The use of clamps extending from the resected surface over the bone lip removes the need for screws or pins, which could damage the femoral neck.

Typically, the bone lip around the initial resected surface is more pronounced in the anterior and posterior plane and tapers into the neck portion. Consequently, it can be preferable to couple the surgical jig to the resected surface such that the clamps extend over the bone lip anteriorly and posteriorly. The natural taper of the bone lip allows the surgical jig to tighten down onto the resected surface to provide base for adjusting the axis and position of the alignment guide.

FIG. 1 illustrates a surgical jig in accordance with an embodiment of the present invention coupled to a resected end of a femur 2. The femur 2 has been partially resected through a lower portion of the femoral head to leave a resected surface 4 at least partially surrounded by a bone lip 6. The bone lip 6 comprises a portion of the femoral head merging into the femoral neck 8. Consequently, the bone lip 6 tapers inwardly below the resected surface 4.

The surgical jig comprises a platform 10 supported on the resected surface 4. The platform 10 is coupled to a pair of parallel rails 12 extending across the resected surface 4. The platform 10 is arranged to slide along rails 12. The platform is held in position along the rails by being compressed against the resected surface, as will be described below. The rails 12 terminate at each end at side frames 14. The rails 12 are extendable so that the distance between the side frames 14 can be adjusted, as will be described below with reference to FIG. 2. Specifically, the rails 12 incorporate a ratchet mechanism for locking the rails in position upon the resected surface.

Each side frame 14 incorporates a clamp 16 to engage the bone lip 6. In particular, the clamps 16 are arranged to hook underneath the bone lip 6 when the side frames 14 are drawn together. As the bone lip 6 tapers inwardly away from the resected surface 4 drawing the side frames 14 together causes the clamps 16 to travel downwards along the bone surface away from the resected surface 4. Consequently, the platform 10 presses against the resected surface 4. The clamps 16 may terminate in a point to reduce the risk of sliding contact between the clamps 16 and the underside of the bone lip 6.

Advantageously, the clamps 16 do not engage the femoral neck 8 and so no damage is done to the femoral neck (which, according to the type of prosthesis to be implanted, may be preserved). The initial resection is performed sufficiently close to the end of the bone that the bone lip will later be removed so any damage to the bone lip is immaterial. The bone lip is generally more pronounced anteriorly and posteriorly and so preferably the clamps 16 are positioned to engage these portions of the bone lip. FIG. 1 illustrates only two clamps. It will be appreciated that in alternative embodiments of the present invention there may be more than one clamp supported by each side frame. For instance, one side frame may have two clamps with the second side frame having a single clamp to form a V shaped attachment.

The surgical jig further comprises an alignment guide 18. The alignment guide 18 comprises a tube arranged to receive a guide pin (not illustrated). The alignment guide 18 is coupled to the platform 10 such that it can pivot relative to the platform 10. The centre of rotation of the alignment guide 18 is arranged to coincide with the resection surface 4, as will be described in greater detail with reference to FIG. 2. The alignment guide 18 can pivot relative to the platform 10 in two orthogonal directions. The longitudinal axis of the alignment guide 18 defines an axis extending into the resected surface 4. A guide pin inserted into the alignment guide 18 can be inserted through the alignment guide 18 and into the end of the bone. Given that the platform 10 can translate across the resected surface 4 by sliding along the rails, and the alignment guide 18 can pivot relative to the platform 10, the axis defined by the alignment guide 18 can be adjusted to coincide with the femoral neck axis or at a given linear or angular offset relative to the femoral neck axis.

Figure 2:
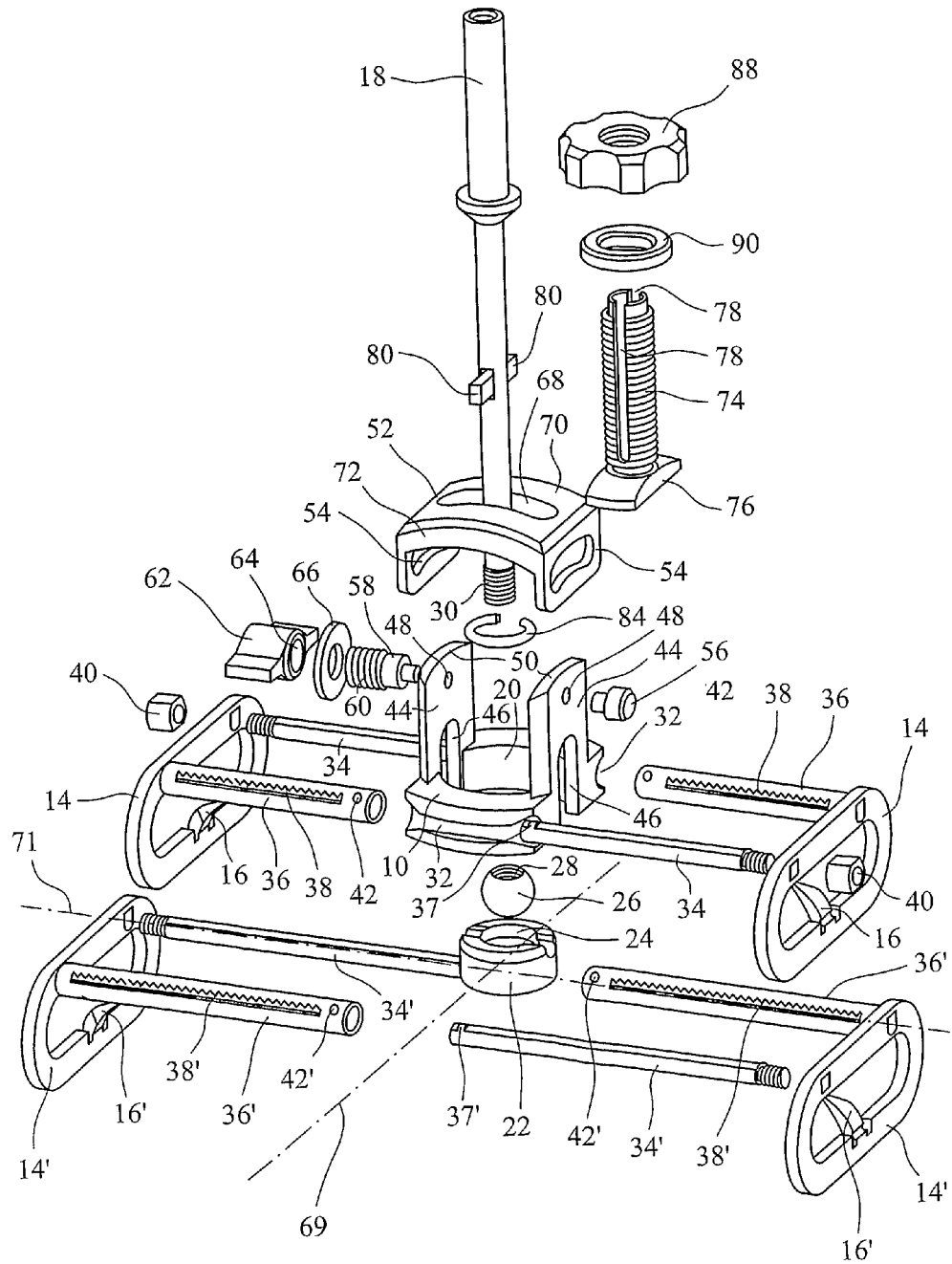
FIG. 2 illustrates an exploded view of the surgical jig of FIG. 1.

Referring now to FIG. 2, this illustrates an exploded view of the surgical jig of FIG. 1. Platform 10 comprises a generally tubular portion 20 having a generally flat underside to be supported upon the resected surface. The generally tubular portion is arranged to receive a circular foot 22 such that the foot 22 can slide within the tubular portion 20 towards and away from the resected surface 4. The foot 22 has a generally spherical cavity 24 arranged to receive a ball joint 26 such that the ball joint 26 can rotate within the cavity 24. Ball joint 26 is retained within cavity 24 by a split ring 84 which fits within an annular recess at the upper edge of the cavity 24 and is held in place under compression against the annular recess. The annular recess incorporates slots which assist in removing or replacing the split ring 84. The ball joint 26 has a threaded bore 28 arranged to couple to an exterior thread 30 at a first end of the alignment guide 18. The alignment guide 18 can therefore pivot relative to the platform 10 about a centre of rotation coincident with the underside of the foot 22, and therefore positioned upon the resected surface 4. As the centre of rotation of the alignment guide 18 is positioned upon the bone surface, when the alignment guide 18 pivots from a position in which it extends normally from the surface of the bone the foot 22 slides across the resected surface 4 within tubular portion 20 of the platform 10. The tubular portion 20 has a larger diameter than the diameter of the foot 22 so that the foot 22 can shift position upon the resected surface 4 without the platform 10 needing to move.

Platform 10 further comprises channels 32 arranged to receive rails 12 such that the platform can slide along the rails 12. Each rail 12 comprises a rod 34 and a sleeve clamp 36 coupled to a respective side frame 14. Each rod 34 is arranged to be received within the corresponding sleeve clamp 36. Each sleeve clamp 36 comprises a ratchet slot 38 incorporating ratchet teeth. The rods 34 are arranged to tilt within the sleeves 36 when the rods 34 are inserted into the sleeves 36 as the surgical jig is coupled to the end of a bone. This tilting of the rods 34 causes a ratchet tooth 37 at the end of each rod 24 to engage the ratchet teeth within the corresponding ratchet slot 38. To later release the rods 34 from sleeves 36 (to decouple the surgical jig from the end of the bone) the ratchet tooth 37 for each rail 12 is depressed so that it is released from the ratchet slot 38. Each rod 34 is coupled to a side frame 14 by a nut 40 such that each side frame 14 supports a sleeve clamp 36 and a rod 34. Each sleeve clamp 36 incorporates a capture pin 42 at its open end. The capture pins 42 extend inwardly such that when the rails 12 are extended the capture pins 42 engage the ratchet tooth 37 at the end of each rod 34 to prevent the rods 34 from fully disengaging from the sleeves 36.

FIG. 2 further illustrates a second set of side frames 14', sleeve clamps 36' and rods 34' for which the sleeve clamps 36' and rods 34' are extended in order to accommodate larger diameter resected bones. It will be understood that these components are used in place of, and not in addition to, the smaller illustrated side frames 14, sleeve clamps 36 and rods 34.

The platform 10 further comprises upwardly extending side portions 44 incorporating side cut outs 46 which allow the surgeon to have a better view of the cut bone surface when positioning the alignment guide 18. Each side portion 44 has a hole 48 in an upper part. An upper edge 50 of each side portion 44 is curved. The surgical jig further comprises a guide frame 52 arranged to fit over the side portions 44. The guide frame 52 comprises first and second curved slots 54. When the guide frame 52 is in position over the side portions 44 of the platform 10 a pin 56 can be passed through a first slot 54 to engage hold 48. The diameter of the portion of pin 56 outside of hole 48 is equal to the width of slot 54. Similarly, a second pin 58 is arranged to pass through a second slot 54 and the diameter of a portion of pin 58 outside of hole 48 is equal to the width of slot 54. When assembled, the guide frame 52 can slide over pins 56, 58. Pins 56, 58 may be welded into holes 48 to hold the pins in position.

Pin 58 further comprises an exterior threaded portion 60. The surgical jig further comprises a first locking nut 62 having a corresponding interior threaded portion 64 and a washer 66. The first locking nut 62 comprises an exterior surface arranged to be easy to grasp and turn. FIG. 2 illustrates a different shape of first locking nut 62 compared with FIG. 1, although functionally they are the same. When the first locking nut 62 is tightened over the threaded portion of pin 58 the washer 66 bears against the guide frame 52, which in turns bears against a side portion 44 of platform 10 preventing the guide frame 52 from sliding relative to the platform 10.

Guide frame 52 further comprises a further slot 68 and the alignment guide 18 is arranged to pass through slot 68. When the surgical jig is assembled the alignment guide 18 can pivot about the ball joint 26 within slot 68. That is, when the guide frame 52 is locked to the platform 10 by tightening first locking nut 62, slot 68 limits movement of the alignment guide such that it can pivot about a first axis 69. The upper surface 70 of the guide frame 52, which defines the slot 68, is curved with a radius of curvature equal to the distance to the centre of rotation of the alignment guide 18.

Similarly, slots 54 are curved and have a radius of curvature equal to the distance to the centre of rotation of the alignment guide 18. When first locking nut 62 is relaxed the guide frame 52 can pivot about the centre of rotation of the alignment guide 18 such that pins 56, 58 travel along slots 54 allowing the alignment guide 18 to pivot about a second axis 71 orthogonal to the first axis 69. The guide frame 52 further comprises skirt portions 72 to limit movement of the guide frame about the second axis 71.

The surgical jig further comprises a threaded sleeve 74 arranged to slide over the alignment guide 18. The threaded sleeve 74 has a flange 76 at a first end which, when the jig is assembled, is seated underneath the guide frame 52. The threaded sleeve 74 has slots 78 arranged to receive lugs 80 protruding from opposite sides of the alignment guide 18 such that the threaded sleeve 74 can not rotate about the alignment guide 18. The surgical jig further comprises a compression spring 82 (not shown in FIG. 2) which, when assembled, is under compression between the threaded sleeve 74 and the ball joint 26. The compression spring 82 biases the threaded sleeve 74 upwards such that it bears against the underside of the guide frame 52.

A second locking nut 86 (not shown in FIG. 2) engages the threaded sleeve 74 and bears against the upper surface 70 of the guide frame 52 to lock the alignment guide 18 in position and prevent further rotation of the alignment guide 18 about the first axis 69.

The surgical jig further comprises a third locking nut 88 and washer 90 arranged to pass over the alignment guide 18 and lock to the threaded sleeve 74 above the lugs 80. Tightening third locking nut 88 over the threaded sleeve 74 causes the alignment guide to travel downwards through the platform 10 such that the foot 22 bears against the resected surface 4.

When the surgical jig is removed from the end of a bone the alignment guide 18 can slide downwards through the threaded sleeve 74 until lugs 80 come to rest against the second locking nut 86. Additionally, movement of the alignment guide 18 is limited by flange 92 shown in FIG. 2, or the equivalent shoulder 94 shown in FIG. 1, coming to rest against the upper part of threaded sleeve 74.

A method of using the surgical jig to determine an axis extending into the end of a bone will now be described. The bone may in particular be a femur and the required axis to be determined using the surgical jig extends into the head of the femur along the femoral neck axis or at a required offset to the femoral neck axis.

The first step is to resect the head of the femur. This may be done while the femoral head is engaged in the acetabulum or alternatively when the hip joint is dislocated. The resection is performed manually by visual inspection. The resection should be performed at a position upon the head/neck junction such that a bone lip will be formed extending at least partially around the resected surface. Furthermore, the resection should be performed sufficiently close to the end of the femur such that later shaping of the end of the femur will remove the entire resected surface (so that there is no requirement for the resected surface to be accurately aligned).

The optimal entry point for an axis extending into the end of the bone is then determined. This may be the point at which the femoral neck axis exits the resected surface, or may be offset from this position. A guide pin is then inserted into the end of the bone by around 1 mm to 2 mm and extending from the resected surface approximately normally.

The surgical jig can then be positioned over the resected surface 4 by sliding the alignment guide 18 over the guide pin such that platform 10 rests upon the resected surface 4 and the side frames 14 overlap the sides of the resected surface 4. The surgical jig may then be rotated until the clamps 16 are aligned with portions of the bone lip 6 providing a suitable attachment. Typically, the bone lip 6 is more pronounced anteriorly and posteriorly and so by positioning the clamps 16 at these portions a more secure attachment can be achieved.

Once the surgical jig is positioned over the bone so that the platform 10 is supported on the resected surface 4 the rails 12 may be shortened by feeding rods 34 into sleeve clamps 36 until clamps 16 hook underneath the bone lip 6 to secure the platform 10 to the resected surface 4. The platform 10 and the foot 22 may then be compressed against the resected surface 4 by tightening third locking nut 88. The angular position of the alignment guide 18 relative to the platform 10 is then adjusted by rotating the alignment guide 18 about the first axis 69. Once in position about the first axis 69, locking nut 62 is tightened to prevent guide slot 54 sliding further along pins 56, 58. The angular position of the alignment guide 18 relative to the platform 10 is then further adjusted by rotating the alignment guide 18 about the second axis 71. Once in position about the second axis 71, locking nut 86 is tightened to comprise the guide frame 52 against the threaded sleeve to prevent further movement of the alignment guide 18 within slot 68.

The centre of rotation about both the first and the second axis 69, 71 is positioned upon the resected surface 4 at a central position within the platform 10. Consequently, the axis can be rotated about the first and second axes 69, 71 without affecting the position of the insertion point.

Once the alignment guide 18 has been adjusted and locked in position, third locking nut 88 is further tightened. This compresses the foot 22 against the resected surface. This further secures the alignment guide 18 in position. The guide pin is then driven through the alignment guide 18 the required distance into the end of the bone along the determined axis.

Finally the surgical jig may be released from the bone by extending rails 12 to release the clamps 16 and sliding the jig over the guide pin. The guide pin remains inserted in the end of the bone and is used to guide further surgical instruments for shaping the end of the bone. For instance, a cannulated drill may pass over the guide pin for forming a bore into the end of the bone along the femoral axis.

All the major components of the jig may be made from surgical stainless steel, although other bio-compatible materials can be used, such as plastics.

The present invention has been primarily described with reference to the insertion of a guide pin into the end of a femur aligned with the femoral neck axis. However, it will be readily apparent that the present invention may be used to determine a reference axis extending into the end of any long bone for which an initial resection has been performed leaving at least a partial bone lip extending around the resected surface.

Further modifications and applications of the present invention will be readily apparent to the appropriately skilled person from the teaching herein, without departing from the scope of the appended claims.

The invention claimed is:

1. A surgical jig for determining an axis extending into the end of a bone having a resected surface, the bone having a resected surface, the bone tapering away from the resected surface to form a bone lip that extends around at least a part of the resected surface, the jig comprising:
    a platform comprising a foot having an underside, the underside configured to be positioned upon the resected surface of the bone;
    a first frame and a second frame connected to the platform, each of the first frame and the second frame having a lower portion that extends below the underside of the foot when the foot is positioned on the resected surface;
    a first clamp coupled to the lower portion of the first frame and a second clamp coupled to the lower portion of the second frame such that the first clamp engages a first portion of the bone lip and the second clamp engages a second portion of the bone lip when the foot is positioned on the resected surface; and
    an alignment guide having a proximal end and a distal end, the elignment guide defining a guide axis, wherein the platform has a bore extending through the platform to the resected surface and wherein the foot is slidably received within the platform bore, the foot being pivotably coupled to the alignment guide.

2. The surgical jig of claim 1, wherein the first clamp comprises a hook attached to the first frame and the second clamp comprises a hook attached to the second frame.

3. The surgical jig of claim 2, wherein the first and second frames are adjustably coupled to one another together via at least one rail arranged to pass over the resected surface of the bone when the foot is positioned on the resected surface, and wherein the platform is slidably coupled to the at least one rail such that the distal end of the alignment guide is translatable across the resected surface.

4. The surgical jig of claim 3, wherein the at least one rail comprises a ratchet for moving the first frame and the second frame relative to one another between a first position, whereat the distance between the first frame and the second frame greater than the width of the resected surface of the bone, and a second distance that is less than the first distance, whereat the first clamp engages a first portion of the bone lip and the second clamp engages a second portion of the bone lip.

5. The surgical jig of claim 1, wherein the alignment guide comprises a tube arranged to receive a guide pin passing through the alignment guide into the end of the bone along the guide axis.

6. The surgical jig of claim 1, wherein the alignment guide is coupled to the platform such that, when the foot is positioned on the resected surface, the alignment guide is rotatable about a center of rotation that is located on the resected surface.

7. The surgical jig of claim 1, wherein the foot slides from a third position within the platform bore to a fourth position when the alignment guide pivots relative to the platform about the center of rotation of the alignment guide.

8. The surgical jig of claim 1, wherein the surgical jig further comprises a guide frame arranged to lock the position of the alignment guide relative to the platform.

9. The surgical jig of claim 8, wherein the guide frame has a first slot through which the alignment guide passes, the first slot restricting movement of the alignment guide to rotation about a first axis.

10. The surgical jig of claim 9, wherein the guide frame comprises a portion that defines the first slot, the portion being curved and defined by a constant radius of curvature extending from the center of rotation of the alignment guide.

11. The surgical jig of claim 9, wherein the surgical jig further comprises a threaded sleeve that is disposed about the alignment guide and configured to pass through the first slot, a flange extending from the distal end of the threaded sleeve, and a first locking nut arranged to engage the threaded sleeve such that edge portions of the guide frame adjacent the first slot can be trapped between the flange and the first locking nut to prevent further rotation of the alignment guide about the first axis.

12. The surgical jig of claim 9, wherein the guide frame has a second slot, and further comprising a pin extending from the platform, the pin being configured to pass through the second slot such that the guide frame is slidably coupled to the platform and sliding motion of the second slot over the pin causes the alignment guide to rotate about a second axis.

13. The surgical jig of claim 12, wherein the second slot has a center line that is curved and is defined by a radius of curvature equal to the distance from the center of the second slot to the resected surface of the bone.

14. The surgical jig of claim 13, wherein the pin comprises a threaded portion and further comprising a second locking nut arranged to engage the threaded portion of the pin such that edge portions of the second slot can be trapped between the platform and the second locking nut to prevent further rotation of the alignment guide about the second axis.

15. The surgical jig of claim 11, wherein the threaded sleeve has a slot and further comprising a lug sized to be disposed within the slot.

* * * * *

UNITED STATES PATENT AND TRADEMARK OFFICE
CERTIFICATE OF CORRECTION

Page 1 of 1

PATENT NO.         : 8,500,743 B2
APPLICATION NO.    : 13/141103
DATED              : August 6, 2013
INVENTOR(S)        : Alec Birkbeck, James Brooks and Andrew Burton It is certified that error appears in the above-identified patent and that said Letters Patent is hereby corrected as shown below:

In the claims, Column 9, Claim 1, Line 47,

Delete "elignment" and replace with -- alignment --

Signed and Sealed this
Sixteenth Day of September, 2014

Michelle K. Lee
*Deputy Director of the United States Patent and Trademark Office*